(12) United States Patent
Chowdhury et al.

(10) Patent No.: US 6,900,257 B2
(45) Date of Patent: May 31, 2005

(54) ANTISTATIC AGENTS AND POLYMER COMPOSITIONS DERIVED THEREFROM

(75) Inventors: Sanjoy Kumar Chowdhury, Bangalore (IN); Theodorus Lambertus Hoeks, AS Bergen op Zoom (NL)

(73) Assignee: General Electric Company, Schenectdy, NY (US)

( * ) Notice: Subject to any disclaimer, the term of this patent is extended or adjusted under 35 U.S.C. 154(b) by 152 days.

(21) Appl. No.: 10/064,676

(22) Filed: Aug. 6, 2002

(65) Prior Publication Data

US 2004/0030015 A1 Feb. 12, 2004

(51) Int. Cl.$^7$ ................................................. C08K 3/34
(52) U.S. Cl. ..................... 524/186; 524/131; 524/132; 524/154; 524/261
(58) Field of Search ................................ 524/186, 132, 524/154

(56) References Cited

U.S. PATENT DOCUMENTS

| | | | |
|---|---|---|---|
| 3,141,898 A | * 7/1964 | Dyke | .......................... 556/428 |
| 4,093,589 A | 6/1978 | Factor et al. | |
| 4,450,249 A | 5/1984 | Schmidt et al. | .............. 524/132 |
| 4,943,380 A | 7/1990 | Sugiura et al. | |
| 4,973,616 A | 11/1990 | Govindan | |
| 5,430,166 A | * 7/1995 | Klein et al. | .................. 556/428 |
| 5,449,709 A | 9/1995 | Imae et al. | ................... 524/154 |
| 5,468,793 A | 11/1995 | Ward et al. | |
| 5,668,202 A | 9/1997 | Hirata et al. | ................. 524/154 |
| 6,372,829 B1 | 4/2002 | Lamanna et al. | ............. 524/99 |

FOREIGN PATENT DOCUMENTS

| | | | | |
|---|---|---|---|---|
| EP | 0 363 094 B1 | 8/1993 | ......... | C07C/211/62 |
| EP | 0897950 | 7/1998 | | |
| EP | 0 873 986 A1 | 10/1998 | ......... | C07C/215/90 |
| EP | 0 905 183 A1 | 3/1999 | ............ | C08K/5/42 |
| GB | 1030888 | 5/1966 | | |
| JP | HEI 4-183775 | 6/1992 | | |
| WO | WO 84/02798 | 7/1984 | ........... | G11B/23/04 |
| WO | WO 90/05129 | 5/1990 | ......... | C07C/215/40 |
| WO | WO 01/25326 A1 | 4/2001 | | |
| WO | WO 01/49925 A1 | 7/2001 | | |

OTHER PUBLICATIONS

English Abstract of EP 0 023 650, published on May 22, 1984.

International Search Report, International Application No. PCT/US 03 19602; International Filing Date Jun. 17, 2003, Date of Mailing Sep. 26, 2003.

JP 7331231. Publication date: Dec. 19, 1995. English Abstract. 1 page.

JP0897950. Publication date: Feb. 24, 1999. English Abstract. 1 page.

Paul, Raji K., et al. "Melt/ solution processable conducting polyaniline with novel sulfonic acid dopants and its thermoplastic blends". Synthetic Metals. vol. 114. pp. 27–35. 2000.

Seth, S.C., et al. "Studies in the Cashewnut Shell Liquid: Part II– Anionic Surface Active Agents from Cardanol. Tetrahydrocardanol & Their Derivatives". Indian J. Technol.. vol. 1. pp. 348–355. Sep. 1963.

JP200095970. Publication Date: Apr. 4, 2000. English Abstract. 1 page.

JP0023650. Publication Date: May 22, 1984. English Abstract. 1 page.

Bajaj. P., et al. "Antistatic and Hydrophilic Synthetic Fibers: A Critique". J.M.S. Rev. Macromol. Chem. Phys., C40 (2&3), pp. 105–138, 2000.

Paul, Raji. K., et al. "Thermal properties of processable polyaniline with novel sulfonic acid dopants". Polymer International. vol. 50. pp. 381–386. 2001.

\* cited by examiner

*Primary Examiner*—Katarzyna Wyrozebski

(57) ABSTRACT

An antistatic additive comprises a quaternary onium organosilicon compound having the formula (I)

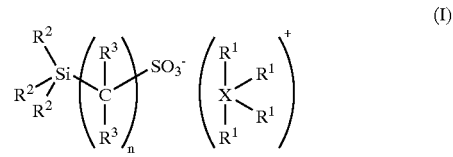

(I)

wherein each $R^1$ independently comprises an aliphatic or aromatic functional groups that may be substituted or unsubstituted; X comprises phosphorus or nitrogen; each $R^2$ independently comprises an aliphatic or aromatic functional group that may be substituted or unsubstituted; each $R^3$ independently comprises a hydrogen or an aliphatic or aromatic functional group that may be substituted or unsubstituted; and "n" has a value of about 1 to about 20.

31 Claims, No Drawings

ANTISTATIC AGENTS AND POLYMER COMPOSITIONS DERIVED THEREFROM

BACKGROUND OF INVENTION

This disclosure relates to new antistatic additives, polymer compositions comprising these additives, as well as methods of making these additives and polymer compositions.

Antistatic agents constitute a unique class of polymer additives. They prevent an accumulation of static electricity on the surface of an article fabricated of the polymer. They also offer aesthetic values by preventing the accumulation of surface dust on the article. For example, lenses of automotive headlamps are typically made of polymers, such as polycarbonates, which have a desirable combination of heat stability, dimensional stability, transparency, and ductility. In the past, the optics system (also sometimes called "Fresnel") necessary to properly focus the headlight beam on the road did not have a smooth profile. Consequently, the dust that accumulated on the lens surface, either during fabrication, or during the service life of the headlamp, was not conspicuously visible. But as the automotive industry moves towards lenses with a smoother profile, the accumulated dust becomes more easily visible, therefore leading to aesthetics issues.

Similarly mitigation of static charge buildup is important in conveyor belt design. Conveyor belts are typically made mostly of synthetic polymeric materials. Use of plastic in conveyor belts has led to several distinct advantages in conveyor belt technology, such as cleanliness, reliability, decreased noise, low cost to lifetime ratio, modularity, and flexibility. As a result of these advantages, plastics-based conveyor systems are being used in hyper clean (class 100 or higher) environments essential for the manufacture of advanced electronics products and systems. But as product dimensions and tolerances approach sub-micron levels, electrostatic discharge, a phenomenon inherent of plastic materials, poses increasing problems to the high technology manufacturers that use plastic conveyor components. The buildup of surface charge results in secondary dirt contamination, which has undesirable consequences, especially for precision, high technology electronic components.

Antistatic agents may be applied in two ways: externally and internally. External antistatic agents are applied by spraying the surface, or dipping the polymeric material in a medium containing the antistatic agent. Internal antistatic agents are added to the polymer before processing. For this reason, internal antistatic agents have to be thermally stable and preferably migrate to the surface during processing. Additionally, the incorporation of the antistatic agent should not diminish desirable characteristics of the polymeric material such a transparency and glass transition temperature (Tg). Several types of antistatic agents are available, but agents with improved properties, such as processability, thermal stability and/or resin compatibility are needed.

It is therefore desirable to identify more effective antistatic agents as additives that can be incorporated into polymers without adversely affecting the physical and chemical properties of the resulting polymer compositions.

SUMMARY OF INVENTION

An antistatic additive comprises a quaternary onium organosilicon compound having the formula (I)

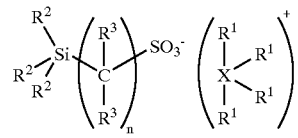

(I)

wherein each $R^1$ independently comprises an aliphatic or aromatic functional groups that may be substituted or unsubstituted; X comprises phosphorus or nitrogen; each $R^2$ independently comprises an aliphatic or aromatic functional group that may be substituted or unsubstituted; each $R^3$ independently comprises a hydrogen or an aliphatic or aromatic functional group that may be substituted or unsubstituted; and "n" has a value of about 1 to about 20.

In another embodiment of the disclosure, an antistatic polymer composition comprises a polymer and a quaternary onium organosilicon compound having the formula (I)

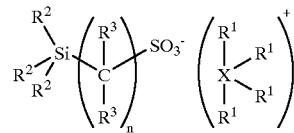

(I)

where $R^1$, X, $R^2$, $R^3$ and "n" are as previously defined.

Still another embodiment is a method of making an antistatic quaternary onium organosilicon compound comprising contacting a solution comprising a first solvent and an organosilicon monosulfonic salt having the formula (II)

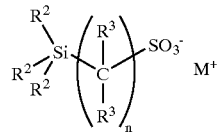

(II)

wherein each $R^2$ independently comprises an aliphatic or aromatic functional group that may be substituted or unsubstituted; each $R^3$ independently comprises a hydrogen or an aliphatic or aromatic functional group that may be substituted or unsubstituted; and "n" has a value of about 1 to about 20 with an acidic medium to generate the corresponding free sulfonic acid; contacting the free sulfonic acid with a quaternary compound to form a mixture, extracting the mixture with a second solvent to provide a solution of a quaternary onium organosilicon compound having the formula (I)

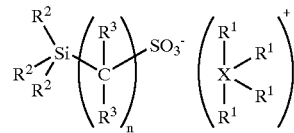

(I)

wherein each $R^1$ independently comprises an aliphatic or aromatic functional groups that may be substituted or unsubstituted; X comprises phosphorus or nitrogen; each $R^2$ independently comprises an aliphatic or aromatic functional group that may be substituted or unsubstituted; each $R^3$ independently comprises an aliphatic or aromatic functional group that may be substituted or unsubstituted; and "n" has a value of about 1 to about 20; and evaporating substantially all the solvent from the solution of quaternary onium organosilicon compound.

In another embodiment, a method of making an antistatic thermoplastic polymer composition comprises combining a quaternary onium organosilicon compound with a thermoplastic resin in melt, wherein the organosilicon compound is represented by the formula:

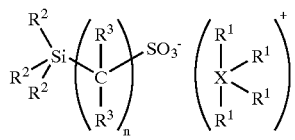
(I)

wherein each $R^1$ independently comprises a substituted or unsubstituted, aliphatic or aromatic functional group; X comprises phosphorus or nitrogen; each $R^2$ independently comprises a substituted or unsubstituted, aliphatic or aromatic functional group; each $R^3$ independently comprises a substituted or unsubstituted, aliphatic functional group, substituted or unsubstituted, aromatic functional group or a hydrogen; and "n" has a value of about 1 to about 20.

In another embodiment, a method of making an antistatic thermoplastic polymer molding composition comprises dry-blending a quaternary onium organosilicon compound with a thermoplastic polymer, wherein the organosilicon compound is represented by the formula:

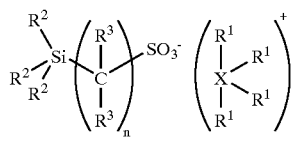
(I)

wherein each $R^1$ independently comprises a substituted or unsubstituted, aliphatic or aromatic functional group; X comprises phosphorus or nitrogen; each $R^2$ independently comprises a substituted or unsubstituted, aliphatic or aromatic functional group; each $R^3$ independently comprises a substituted or unsubstituted, aliphatic functional group, substituted or unsubstituted, aromatic functional group or a hydrogen; and "n" has a value of about 1 to about 20.

DETAILED DESCRIPTION

Quaternary onium organosilicon compounds having the formula (I)

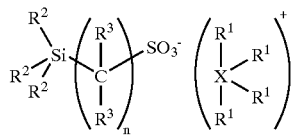
(I)

wherein each $R^1$ independently comprises aliphatic or aromatic functional groups that may be substituted or unsubstituted; X is selected from the group consisting of phosphorus and nitrogen; each $R^2$ independently comprises aliphatic or aromatic functional groups that may be substituted or unsubstituted; each $R^3$ independently comprises a hydrogen or an aliphatic or aromatic functional groups that may be substituted or unsubstituted; and "n" has a value of about 1 to about 20 have great utility as antistatic additives in polymeric compositions, particularly thermoplastic polymeric compositions. The antistatic additives described herein are thermally stable for the cycle times and temperatures generally employed in polymer processing. Polymer compositions comprising the quaternary onium organosilicon compounds maintain their physical properties, such as glass transition temperature, when compared to similar polymer compositions without the quaternary onium organosilicon compounds, even after being formed into the desired shape or article. These advantages make the resulting antistatic polymer compositions valuable in many applications including automotive, electronic, conveyor belt system, and display device applications where effective dissipation of static electricity and/or dust repellency are important requirements. In all embodiments of the disclosure, the term "antistatic" is also meant to imply "antidust".

The $R^1$ groups in the quaternary onium organosilicon compounds depicted hereinabove can assume a wide variation in their structures as long as the structure of the group or groups does not hinder formation of the quaternary onium organosilicon compound. Each $R^1$ group independently comprises a substituted or unsubstituted, aliphatic or aromatic functional group. Furthermore, there can be various combinations of substituted or unsubstituted, aliphatic or aromatic functional groups. Stated another way, the four $R^1$ groups bonded to X can all be the same, or they can consist of two, three, or four different functional groups.

Useful aliphatic $R^1$ functional groups comprise $C_1$–$C_{18}$ linear or branched alkyl, aralkyl, and cycloalkyl groups. The aliphatic functional group may further comprise one or more heteroatoms. Preferably, $R^1$ is selected from the group consisting of methyl, ethyl, n-propyl, n-butyl, n-pentyl, n-hexyl, n-octyl, n-dodecyl, n-hexadecyl, and n-octadecyl. More preferably, $R^1$ is n-butyl. Examples of organic groups containing oxygen atoms include hydrocarbon groups substituted with hydroxyl or alkoxy group. More specifically, the heteroatom containing group includes, but is not limited to hydroxyalkyl groups, such as hydroxymethyl, hydroxyethyl, hydroxypropyl, hydroxybutyl, hydroxypentyl, hydroxyhexyl, hydroxyheptyl, and hydroxyoctyl; and alkoxyalkyl groups, such as methoxymethyl, ethoxymethyl, ethoxyethyl, n-propoxymethyl, isopropoxymethyl, n-butoxymethyl, n-butoxyethyl, isobutoxyethyl, polyalkylene glycol, and the like, including mixtures thereof.

Useful aromatic $R^1$ functional groups comprise $C_6$–$C_{14}$ substituted or unsubstituted aromatic groups. Unsubstituted aromatic groups may be selected from the group consisting of phenyl, indenyl, biphenyl, 1-naphthyl, 2-naphthyl, anthracenyl, and fluorenyl. Substituted aromatic groups may be selected from the group consisting of halophenyl, polyhalophenyl, chlorophenyl, dichlorophenyl, trichlorophenyl, bromophenyl, fluorophenyl, difluorophenyl, alkoxyphenyl, alkoxycarbonylphenyl, nitrophenyl, cyanophenyl, alkylphenyl, polyalkylphenyl, tolyl, xylyl, benzyl, isopropylphenyl, isobutylphenyl, chloronaphthyl, methyinaphthyl, and isopropylnaphthyl. The aromatic functional group may further comprise one or more heteratom containing substituents.

Examples of the $(R^1_4X)^+$ fragment of the quaternary onium organosilicon compound include, but are not limited to, tetramethylammonium, tetramethylphosphonium, tetraethylammonium, tetraethylphosphonium, tetra-n-butylammonium, tetra-n-butylphosphonium, tetra-n-pentylammonium, tetra-n-pentylphosphonium, tetra-n-hexylammonium, tetra-n-hexylphosphonium, tetra-n- heptylammonium, tetra-n-heptylphosphonium, tetra-n-octylammonium, tetra-n-octylphosphonium, tetraphenylammonium, tetraphenylphosphonium, methyltriphenylammonium, methyltriphenylphosphonium, benzyltriphenylammonium, benzyltriphenylphosphonium, benzyltrimethylammonium, benzyltrimethylphosphonium, benzyltriethylammonium, benzyltriethylphosphonium, (n-hexadecyl)(tri-n-butyl)ammonium, (n-hexadecyl)(tri-n-butyl)phosphonium, (n-octadecyl)trimethylammonium, (n-octadecyl)trimethylphosphonium, (n-hexadecyl)trimethylammonium, (n-hexadecyl)trimethylphosphonium, methyl(tri-n-octyl)ammonium, methyl(tri-n-octyl)phosphonium, methyl(tri-n-decyl)ammonium, methyl(tri-n-decyl)phosphonium, (tri-n-butyl)(n-tetradecyl)ammonium, (tri-n-butyl)(n-tetradecyl)phosphonium, ethyl(tri-n-butyl)ammonium, and ethyl(tri-n-butyl)phosphonium. In a preferred embodiment, the $(R^1)_4X^+$ fragment is selected from the group consisting of tetra-n-butylammonium and tetra-n-butylphosphonium.

Each $R^2$ group bonded to silicon independently comprises substituted or unsubstituted aliphatic or aromatic, substituted or unsubstituted groups. In other words, the three $R^2$ groups bonded to silicon may comprise the same functional group or different functional groups. Useful $R^2$ groups comprise substituted or unsubstituted $C_1$–$C_{18}$ linear and branched alkyl radicals, aralkyl, and cycloalkyl radicals. Aliphatic $R^2$ groups may also comprise one or more heteroatoms. Preferably, $R^2$ is selected from the group consisting of methyl, ethyl, n-propyl, n-butyl, n-pentyl, n-hexyl, n-octyl, n-dodecyl, n-hexadecyl, and n-octadecyl. More preferably, $R^2$ is a methyl radical. $R^2$ can also be a fluorinated monovalent hydrocarbyl group, such as 3,3,3-trifluoropropyl and other perfluoroalkylethyl groups, alpha, alpha, alpha-trifluoromethylphenyl, pentafluorophenyl, and the like.

Useful aromatic $R^2$ functional groups typically comprise substituted or unsubstituted $C_6$–$C_{14}$ aromatic groups. Exemplary aromatic functional groups include phenyl, indenyl, biphenyl, 1-naphthyl, 2-naphthyl, anthracenyl, and fluorenyl. Exemplary substituted aromatic functional groups include halophenyl, polyhalophenyl, chlorophenyl, dichlorophenyl, trichlorophenyl, bromophenyl, fluorophenyl, difluorophenyl, alkoxyphenyl, alkoxycarbonylphenyl, nitrophenyl, cyanophenyl, alkylphenyl, polyalkylphenyl, tolyl, xylyl, benzyl, isopropylphenyl, isobutylphenyl, chloronaphthyl, methylnaphthyl, isopropylnaphthyl, and the like. The aromatic functional group may also comprise one or more heteroatom containing substituents.

The $R^3$ groups of the $(R^3{}_2C)_n$ fragment of the quaternary onium organosilicon compounds comprise substituted or unsubstituted aliphatic or aromatic functional groups as described above with regard to $R^1$ and $R^2$. Additionally, $R^3$ may be hydrogen. The $R^3$ groups may be the same or different. Preferably $R^3$ is selected from the group consisting of methyl, ethyl, n-propyl, n-butyl, n-pentyl, n-hexyl, n-octyl, n-dodecyl, n-hexadecyl, and n-octadecyl. More preferably, $R^3$ is hydrogen. The "n" in the general formula of the quaternary onium organosilicon compounds has a value of about 1 to about 20. In a particular embodiment, "n" has a value of about 3.

In a preferred embodiment, the quaternary onium organosilicon compound has the structure where each $R^1$ is an n-butyl radical, X is phosphorus or nitrogen, each $R^2$ is a methyl radical, each $R^3$ is a hydrogen, and "n" has a value in the range from about 2 to about 10. In a particular embodiment, each $R^1$ is an n-butyl radical, X is phosphorus or nitrogen, each $R^2$ is a methyl radical, each $R^3$ is a hydrogen, and "n" has a value of about 3. Preferably X is phosphorous.

The alkali metal "M" in the organosilicon monosulfonic acid salt is selected from the group consisting of lithium, sodium, potassium, rubidium, and cesium. These salts are used as precursors to obtain the corresponding free organosilicon monosulfonic acid. In various embodiments, the acidic medium that is used to generate the free organosilicon monosulfonic acid comprises strong acids.

Examples of strong acids that may be used include sulfuric acid, fluoroalkylsulfonic acids and perfluoroalkylsulfonic acids. In a particular embodiment, the acidic medium comprises a polymeric, strongly acidic ion exchange resin bearing sulfonic acid groups. Suitable examples of polymeric, strongly acidic ion exchange resin bearing sulfonic acid groups include, but are not limited to fluorinated polymeric sulfonic acid resins, such as the Nafion® series of resins (available commercially from Dupont), and sulfonated styrene-divinylbenzene copolymers prepared using from about 0.5 mole percent to about 20 mole percent of divinylbenzene per hundred moles of styrene employed. In particular embodiments, the sulfonated styrene-divinylbenzene copolymers comprise gelular and macroreticular varieties, corresponding to the sulfonated, low and high divinylbenzene-crosslinked styrene copolymers, respectively. An example of a gelular resin is Amberlyst-121 (sulfonated, 4% divinylbenzene-crosslinked polystyrene resin) available commercially from Rohm and Haas Company. An example of a macroreticular resin is Amberlyst-15 (sulfonated, 20% divinylbenzene-crosslinked polystyrene resin), also available commercially from Rohm and Haas Company.

Generally, an excess of the acidic medium over the organosilicon monolsulfonic acid salt is employed to ensure essentially complete conversion to the free organosilicon monosulfonic acid. Essentially complete conversion is herein defined as greater than about 95%, preferably greater that about 98%, and more preferably greater than about 99% complete, based on the starting amount of the organosilicon monosulfonic acid salt. In one embodiment, the acidic medium employed is a sulfonated styrene-divinylbenzene resin, and is used in an amount of about 15 times to about 20 times the number of moles of the alkali metal organosilicon sulfonic acid salt. Higher amounts of the acidic medium can also be employed, but they are generally not required.

In one embodiment, an organosilicon monosulfonic acid salt is contacted with an acidic medium comprising a polymeric acidic resin by introducing a solution comprising the organosilicon monosulfonic acid to the top of a packed bed column containing the acidic resin. The alkali metal ions are exchanged for hydrogen ions in the column such that the liquid stream coming out from the bottom of the column contains the corresponding free organosilicon monosulfonic acid. Alternatively, contacting is effected by pumping the solution from the bottom of the packed bed column and the solution of the product mixture is collected from the top.

Suitable solvents for preparing a solution comprising the organosilicon monosulfonic acid salt comprise water, $C_1$–$C_4$ aliphatic alcohols, tetrahydrofuran, acetonitrile, $C_7$–$C_9$ aromatic hydrocarbons, and mixtures thereof. Generally the presence of water facilitates the alkali metal ion-hydrogen ion exchange process.

The free organosilicon monosulfonic acid composition obtained above is neutralized by contacting it with a quaternary compound comprising $(XR^1{}_4)^+Y^-$, wherein X and $R^1$ are described above, forming a neutralization mixture. Y comprises hydroxide, $OCOR^4$, or $OR^4$, wherein $R^4$ comprises a substituted or unsubstituted aliphatic, carbocyclic or aromatic functional group. These basic quaternary ammonium and phosphonium compounds react with the sulfonic acid group to generate the corresponding quaternary onium organosilicon compounds in the reaction mixture. In a one embodiment, Y is a hydroxide group. In another embodiment, the quaternary compound is selected from the group consisting of tetraethylphosphonium hydroxide, tetra-n-butylphosphonium hydroxide, tetra-n-butylammonium hydroxide, tetra-n-octylphosphonium hydroxide, and tetraphenylphosphonium hydroxide.

The neutralization step is carried out such that the temperature of the reaction mixture is maintained at about 10° C. to about 50° C. in one embodiment, and at about 20° C. to about 30° C. in another embodiment. In another embodiment the reaction is carried out at autogenous temperature. The neutralization process is conveniently carried out by monitoring the pH of the nuetralization mixture. In one embodiment, the pH of the neutralization mixture is about 4 to about 6, while in another embodiment, the pH is about 5 to about 5.5.

The quaternary onium organosilicon sulfonate obtained from the neutralization step is extracted out of the product mixture by using a suitable solvent. Suitable solvents include those that dissolve the quaternary onium organosilicon compound. In some embodiments, suitable solvents comprise halogenated aliphatic and aromatic compounds, aliphatic and aromatic hydrocarbons, cyclic and acylic ethers, and mixtures thereof. In a particular embodiment, a suitable solvent for extraction is chloroform.

The solvent present in the extractant is evaporated such that substantially all the solvent is removed. In one embodiment, "substantially" means an amount which is greater than 90 weight percent (wt. %) removed, in other embodiments, greater than about 98 wt. % removed, in still other embodiments, greater than about 99 wt. % removed, based on the weight of solvent used. In still another embodiment, removal of substantially all the solvent means that no more condensate is obtained in the evaporation process.

The general method described above is applicable for preparing any of the quaternary onium organosilicon compounds described above. In a particular embodiment, the general method is used for preparing tetra-n-butylphosphonium 3-trimethylsilylpropanesulfonate. The solution comprising water and sodium 3-trimethylsilylpropanesulfonate, used for carrying out the sodium ion-hydrogen ion exchange can also comprise $C_1$–$C_4$ aliphatic alcohols, tetrahydrofuran, acetonitrile, $C_7$–$C_9$ aromatic hydrocarbons, and mixtures thereof. The solvent used for extraction of the product in various embodiments comprises halogenated aliphatic and aromatic compounds, aliphatic and aromatic hydrocarbons, cyclic and acylic ethers, and mixtures thereof. Evaporation of the solvent from the extract to isolate the final product can be accomplished under atmospheric pressure or under subatmospheric pressure.

The quaternary onium organosilicon compounds depicted hereinabove have high surface migratory aptitude in polymeric compositions that aids in fast dissipation of localized static charge accumulated on a polymer surface. These compounds possess a polar, hydrophilic onium sulfonate group, and a non-polar, hydrophobic moiety. Although the invention is not limited by any theory of operation, it is believed that the silicon containing hydrophobic moiety enhances migratory aptitude and the polar group attracts ambient moisture to form a layer of water molecules on the polymer surface. These water molecules in turn are hydrogen bonded to each other. Dissipation of localized surface charge occurs through this hydrogen-bonded layer of water molecules, thus leading to antistatic activity.

The quaternary onium organosilicon compounds have high thermal stability based on thermogravimetric analyses (hereinafter referred to as "TGA"). TGA studies show that these compounds do not undergo any significant thermal decomposition even at temperatures of greater than about 300° C., conditions which are generally used for processing polymers. The thermal stability characteristics are comparable to that of tetra-n-butylphosphonium 4-dodecylbenzene sulfonate (CAS: 111503-99-2; commercially available as EPA 202 from Takemoto Oil & Fat Co., Ltd.). Another important characteristic of quaternary onium organosilicon compounds is that they do not adversely affect the physical properties of the compositions to which they are added, such as glass transition temperature of the resulting polymeric compositions.

The quaternary onium organosilicon compounds described above are valuable as antistatic additives for any polymer. Thus they can be used in thermoplastic as well as thermoset polymer compositions. In one embodiment, the polymers that can be used comprise condensation and addition polymers. Depending upon the type of application and the type of polymer, the amount of the quaternary onium organosilicon compound can vary. Polymer compositions typically comprise the quaternary onium organosilicon compound in amounts of about $2.5 \times 10^{-3}$ parts to about 6 parts per 100 parts of the polymer in one embodiment, about $3 \times 10^{-2}$ parts to about 6 parts per 100 parts of polymer in a second embodiment, and about 0.5 parts to about 6 parts per 100 parts of polymer in a third embodiment. Preferred quaternary onium organosilicon compounds are tetra-n-butylphosphonium 3-trimethylsilylpropanesulfonate, tetra-n-butylammonium 3-trimethylsilylpropanesulfonate, and mixtures thereof.

Useful thermoplastic polymers comprises aromatic polycarbonate, polyestercarbonate, polyphenylene sulfide, polyetherimide, polyester, liquid crystalline polyester, polystyrene, polyphenylene ether, polyphenylene ether/styrene polymer blends, polyamide, polyketone, acrylonitrile-butadiene-styrene copolymer, styrene-acrylonitrile copolymer, polyolefin, polyethylene, polypropylene, polyacetal, blends thereof, and blends thereof with other materials, such as for example, glass. Preferred thermoplastic polymers are polycarbonates and polyestercarbonates obtained from polymerization processes, which include melt transesterification, interfacial polymerization, solid state polymerization, and solution and redistribution processes, or combinations thereof.

The polymer composition may further comprise materials such as antioxidants, thermal stabilizers, ultraviolet stabilizers, processing agents, mold release agents, fillers, and flame retardants.

The antistatic polymer compositions may be made using methods known in the art. In particular embodiments, the polymer compositions may be made by methods comprising steps, at least one step of which comprises dry-blending the quaternary onium organosilicon compound with pellets or powder of the thermoplastic resin to produce a polymer composition, melt blending the quaternary onium organosilicon compound with polymer resin in a melt process or solution blending the quaternary onium organosilicon compound with the polymer resin. These techniques are known in the art.

Dry blending represents the process of preparing the polymer composition by mixing all the necessary ingredients before the blended mixture is subjected to a polymer processing step for making articles. Dry blending is performed using techniques that are well known to one skilled in the art. The polymer resin component of the feed is either in a pellet form, powder form, or both. In a particular embodiment the polymer resin component of the feed is in powder form. In various embodiments, the feed for the blending process may also include other materials as additives, as previously described.

Another method of making the polymer composition involves combining the ingredients in melt. Depending upon the quaternary onium organosilicon compound a solvent is optionally used to aid in mixing with the rest of the feed mixture. In some embodiments, the processing equipment may have a devolatilization system to effectively remove volatiles such as solvent during the processing step. Any convenient type of melt processing equipment may be employed and those skilled in the art may choose appropriate equipment without undue experimentation depending upon such factors as the type of polymer to be processed. In various embodiments suitable melt processing equipment includes, but is not limited to, extruders, kneaders, roll-mills and similar equipment.

The polymer composition may be formed into articles or coatings using any methods known in the art such as injection molding, sheet molding, thermoforming, blow molding, and spray coating.

The antistatic compositions find a variety of uses in such applications as in forward lighting assemblies, automotive headlamp lenses, fog lamp lenses, ophthalmic devices, conveyor belt systems, printer devices, and display panel devices for appliances.

The following examples are included to provide additional guidance to those skilled in the art in practicing the claimed disclosure. The examples provided are merely representative of the work that contributes to the teaching of the present application. Accordingly, these examples are not intended to limit the disclosure, as defined in the appended claims, in any manner.

EXAMPLE 1

This example describes the preparation of tetra-n-butylphosphonium 3-trimethylsilylpropanesulfonate.

Tulsion T-42 MP($H^+$), an acidic gel type ion exchange resin was purchased from Thermax Company, India. The resin had moisture content of about 50–52% and an exchange capacity of about 1.8 milliequivalents of $H^+$ per unit volume of resin in the wet state (about 4.9 milliequivalents of $H^+$ per unit volume of resin in the dry state).

A solution of sodium 3-(trimethylsilyl)-1-propanesulfonate (13 grams, 59.5 mmol) dissolved in demineralized water (75 ml) was added dropwise into a short column packed with an excess (15–20 times the molar amount of 3-(trimethylsilyl)-1-propanesulfonate) of Tulsion T-42 MP($H^+$) acidic ion exchange resin. Then the resin bed was washed with water until the pH of the solution eluting from the column was about 5 to 6. The water solution of the free 3-(trimethylsilyl)-1-propanesulfonic acid thus obtained was neutralized with tetra-n-butylphosphonium hydroxide until the pH of the solution was about 5 to 5.5. The resulting mixture was extracted with chloroform (three times) and the combined chloroform washes was washed with water (three times). The chloroform layer was separated, dried with anhydrous sodium sulfate, and concentrated under reduced pressure to remove solvent and other volatiles. The residual material was finally dried at 40° C. and 0.1 mm Hg to afford tetra-n-butylphosphonium 3-(trimethylsilyl)-1-propanesulfonate as a white solid. The yield of the product was 26.9 grams, or 99% of the theoretical amount. Proton NMR spectrum of the compound indicated that it was the desired compound.

EXAMPLE 2

This example describes the preparation of tetra-n-butylammonium 3-trimethylsilylpropanesulfonate.

A solution of sodium 3-(trimethylsilyl)-1-propanesulfonate (9 grams, 41.2 mmol) dissolved in demineralized water (75 ml) was added drop wise into a short column packed with an excess (15–20 times the molar amount of 3-(trimethylsilyl)-1-propanesulfonate) of Tulsion T-42 MP($H^+$) acidic ion exchange resin. Then the resin bed was washed with water until the pH of the solution eluting from the column was about 5 to 6. The water solution of the free 3-(trimethylsilyl)-1-propanesulfonic acid thus obtained was neutralized with tetra-n-butylammonium hydroxide until the pH of the solution was about 5 to 5.5. The resulting mixture was extracted with chloroform (three times) and the combined chloroform washes was washed with water (three times). The chloroform layer was separated, dried with anhydrous sodium sulfate, and concentrated under reduced pressure to remove solvent and other volatiles. The residual material was finally dried at 40° C. and 0.1 mm Hg to afford tetra-n-butylammonium 3-(trimethylsilyl)-1-propanesulfonate as a hygroscopic white solid. The yield of the product was 17.4 grams, or 97% of the theoretical amount. Proton NMR spectrum of the compound indicated that it was the desired compound.

EXAMPLES 3–5

These examples describe the preparation of the plaques and methods for measuring their static decay half time, glass transition temperature and percent transmission.

The aromatic polycarbonate resin used in the examples was a bisphenol A (hereinafter referred to as "BPA") homopolycarbonate resin having an intrinsic viscosity of about 0.46 deciliters per gram, as measured in dichloromethane at 20° C. The polycarbonate was melt-blended with 15 grams of antistatic and/or antidust agent per kilogram of the molding mixture. The molding mixture also contained 2.7 grams of silicone oil mold release agent per kilogram of molding mixture and 3.9 grams of stabilizers per kilogram of molding mixture, which are not believed to affect the antistatic properties. The molding mixture was molded in a 25 mm twin-screw extruder using an operating temperature of about 285° C. After being extruded through a die orifice, the resulting strands were quenched in water and cut into pellets, which were dried at about 120° C. for about 2 h. The dried pellets were injection molded using a single screw injection-molding machine to produce 10 cm square plaques having a thickness of about 2.5 mm. The maximum temperature for the injection-molding barrel was about 285° C.

The plaques required for carrying out the static decay tests were obtained from the larger plaques prepared above. Each plaque used for the static decay test measured about 78 mm×58 mm×2.5 mm. Prior to the test, the plaques were conditioned at a temperature of about 23° C. and a relative humidity of about 50% for about three days. The static decay tests were carried out on these plaques using a Static Honestmeter, Model S-5109 instrument manufactured by Shishido Electrostatic Ltd. The applied voltage was cut-off when the surface charge attained a fixed value of about 3 kilovolts. Subsequently, the decay of surface charge was followed with time with a detector. The static half decay time (indicated by "$T_{1/2}$") represents the time at which the surface charge reached a value that was half the initial value. The above procedure was repeated for the reference material, EPA 202. Glass transition temperatures (Tg) were measured using a Perkin Elmer Model TGA-7 Thermogravimetric Analyzer. Percent transmission (hereinafter referred to as "%T"), was measured using a Pacific Scientific® Model XL-835 colorimeter. Results are shown in Table 1.

The above process was repeated with a BPA homopolycarbonate molding mixture, but which did not contain an antistatic agent. The resulting plaque was tested for its static half decay time and $T_g$.

TABLE 1

| Example | Antistatic compound | $T_{1/2}$ (Seconds) | $T_g$ (C) | % T |
|---|---|---|---|---|
| 3 | EPA 202 | 132 | 143 | 90 |
| 4 | Tetra-n-butylphosphonium 3-trimethylsilylpropanesulfonate | 92.5 | 139 | 77 |
| 5 | None | >>1000 | 150 | 90 |

*Control.

As can be seen from the preceding examples the quaternary onium organosilicon compound shows significantly better dissipation of surface charge of a polymeric composition without significantly affecting the glass transition temperature.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All patents cited herein are incorporated herein by reference.

What is claimed is:

1. A quaternary onium organosilicon compound having the formula (I):

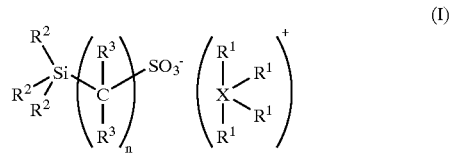

(I)

wherein each $R^1$ independently comprises an aliphatic or aromatic functional group; X is phosphorus; each $R^2$ independently comprises an aliphatic or aromatic functional group; each $R^3$ independently comprises an aliphatic functional group, an aromatic functional group, or a hydrogen; and "n" has a value of 1 to about 20.

2. The compound of claim 1, wherein each $R^1$ is an n-butyl radical, X is phosphorus, each $R^2$ is a methyl radical, each $R^3$ is a hydrogen, and "n" has a value of 2 to about 10.

3. The compound of claim 1, wherein each $R^1$ is an n-butyl radical, X is phosphorus, each $R^2$ is a methyl radical, each $R^3$ is a hydrogen, and "n" has a value of 3.

4. A polymer composition comprising a polymer and a quaternary onium organosilicon compound having the formula (I):

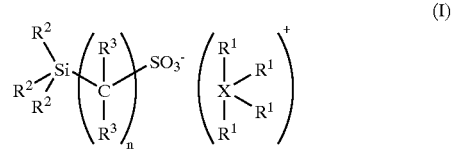

(I)

wherein each $R^1$ independently comprises an aliphatic or aromatic functional group; X comprises phosphorus or nitrogen; each $R^2$ independently comprises an aliphatic or aromatic functional group; each $R^3$ independently comprises an aliphatic functional group, an aromatic functional group, or a hydrogen; and "n" has a value of 1 to about 20.

5. The composition of claim 4, wherein the organosilicon compound is present in an amount of about $2.5 \times 10^{-3}$ parts to about 6 parts per 100 parts of the polymer.

6. The composition of claim 4, wherein the organosilicon compound is present in an amount of about $3 \times 10^{-2}$ parts to about 6 parts per 100 parts of the polymer.

7. The composition of claim 4, wherein the organosilicon compound is present in an amount of about 0.3 parts to about 6 parts per 100 parts of the polymer.

8. The composition of claim 4, wherein the polymer comprises at least one condensation or addition polymer.

9. The composition of claim 8, wherein said polymer comprises at least one aromatic polycarbonate, polyestercarbonate, polyphenylene sulfide, polyetherimide, polyester, polyphenylene ether, polyphenylene ether/styrene polymer blends, polyamide, polyketone, acrylonitrile-butadiene-styrene copolymer, styrene-acrylonitrile copolymer, polyolefin, blends thereof, or blends thereof with other materials.

10. The composition of claim 9, wherein the polycarbonate and polyestercarbonate are obtained from polymerization processes comprising melt transesterification, interfacial polymerization, solid state polymerization, solution, redistribution processes, or combinations thereof.

11. The composition of claim 10, wherein the organosilicon compound comprises

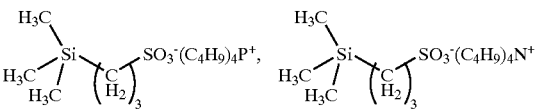

or a mixture thereof.

12. An antistatic article comprising the polymer composition of claim 11.

13. The article of claim 12, wherein the article comprises forward lighting assemblies, automotive headlamp lenses, fog lamp lenses, ophthalmic devices, conveyor belt systems, printer devices, and display panel devices for appliances.

14. A method of making a quaternary onium organosilicon compound comprising:

contacting a solution comprising a first solvent and an organosilicon monosulfonic acid salt having the formula (II)

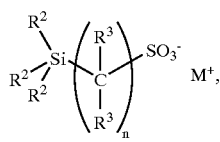

wherein M is an alkali metal, each $R^2$ independently comprises an aliphatic or aromatic functional group; each $R^3$ independently comprises an aliphatic functional group, an aromatic functional group, or a hydrogen; and n is an integer having a value of 1 to about 20; with an acidic medium to generate the corresponding free sulfonic acid composition, contacting the free sulfonic acid composition with a quaternary phosphorus compound to form a neutralization mixture, extracting the neutralization mixture with a second solvent to provide an extractant; and evaporating substantially all the solvent from the extractant to isolate a quaternary onium organosilicon compound having the formula (I):

(I)

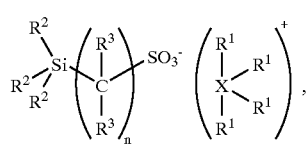

wherein each $R^1$ independently comprises an aliphatic or aromatic functional group; X is phosphorus; each $R^2$ independently comprises an aliphatic or aromatic functional group; each $R^3$ independently comprises an aliphatic functional group, an aromatic functional group, or a hydrogen; and "n" has a value of 1 to about 20.

15. The method of claim 14, wherein the alkali metal comprises lithium, sodium, potassium, rubidium, or cesium.

16. The method of claim 14, wherein the free sulfonic acid composition is contacted with the quaternary compound at a temperature of about 10° C. to about 50° C.

17. The method of claim 14, wherein the free sulfonic acid composition is contacted with the quaternary compound at a temperature of about 20° C. to about 30° C.

18. The method of claim 14, wherein the acidic medium comprises a strong mineral acid, a polymeric acidic ion exchange resins or a combination thereof.

19. The method of claim 18, wherein the acid medium is a polymeric acidic ion exchange resin bearing sulfonic acid groups.

20. The method of claim 14, wherein the quaternary phosphorus compound comprises $P(R^1)_4$—Y, wherein; each $R^1$ independently comprises an aliphatic or aromatic functional group; and Y comprises hydroxide, $OCOR^4$, and $OR^4$, wherein $R^4$ comprises a substituted or unsubstituted, aliphatic or aromatic functional group.

21. The method of claim 20, wherein $R^1$ is n-butyl, and Y is hydroxide.

22. The method of claim 20, wherein the quaternary compound comprises tetraethylphosphonium hydroxide, tetra-n-butylphosphonium hydroxide, tetra-n-octylphosphonium hydroxide, or tetraphenylphosphonium hydroxide.

23. Tho method of claim 14, wherein the pH of the neutralization mixture is about 4 to about 6.

24. The method of claim 14, wherein the pH of the neutralization mixture is about 5 to about 5.5.

25. The method of claim 14, wherein the first solvent comprises water, $C_1$–$C_4$ aliphatic alcohols, tetrahydrofuran, acetonitrile, $C_7$–$C_9$ aromatic hydrocarbons, or mixtures thereof.

26. The method of claim 16, wherein the quaternary onium organosilicon compound is tetra-n-butylphosphonium 3-trimethylsilylpropanesulfonate.

27. A method of making tetra-n-butylphosphonium 3-trimethylsilylpropanesulfonate comprising:

contacting a solution comprising a first solvent and sodium 3-trimethylsilylpropanesulfonate with an acidic ion exchange resin to generate a solution of free 3-trimethylsilylpropanesulfonic acid;

contacting the solution of free 3-trimethylsilylpropanesulfonic acid with tetra-n-butylphosphonium hydroxide to form a mixture having a pH of about 5.0 to about 5.5;

extracting the mixture with a second solvent to form an extractant comprising tetra-n-butylphosphonium 3-trimethylsilylpropanesulfonate; and evaporating substantially all of the solvent from the extractant to isolate tetra-n-butylphosphonium 3-trimethylsilylpropanesulfonate.

28. The method of claim 27, wherein said first solvent comprises water, $C_1$–$C_4$ aliphatic alcohols, tetrahydrofuran, acetonitrile, $C_7$–$C_9$ aromatic hydrocarbons, or mixtures thereof.

29. The method of claim 27, wherein the second solvent comprises halogenated aliphatic and aromatic compounds, aliphatic and aromatic hydrocarbons, cyclic and acylic ethers, or mixtures thereof.

30. A method of making an antistatic thermoplastic polymer composition comprising:

combining a quaternary onium organosilicon compound with a thermoplastic resin in melt, wherein the organosilicon compound is represented by the formula:

(I)

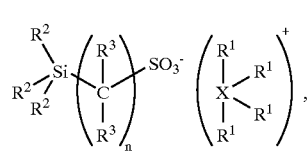

wherein each $R^1$ independently comprises an aliphatic or aromatic functional group; X comprises phosphorus or nitrogen; each $R^2$ independently comprises an aliphatic or aromatic functional group; each $R^3$ independently comprises an aliphatic functional group, aromatic functional group, or a hydrogen; and "n" has a value of 1 to about 20.

31. A method of making an antistatic thermoplastic polymer composition comprising:

dry-blending a thermoplastic polymer with a quaternary onium organosilicon compound, wherein the organosilicon compound is represented by the formula:

(I)

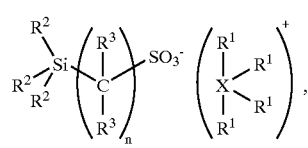

wherein each $R^1$ independently comprises an aliphatic or aromatic functional group; X comprises phosphorus or nitrogen; each $R^2$ independently comprises an aliphatic or aromatic functional group; each $R^3$ independently comprises an aliphatic functional group, aromatic functional group, or a hydrogen; and "n" has a value of 1 to about 20.

* * * * *